US010195336B2

(12) United States Patent
Kogoshi et al.

(10) Patent No.: US 10,195,336 B2
(45) Date of Patent: Feb. 5, 2019

(54) BLOOD PURIFICATION APPARATUS AND PRIMING METHOD THEREOF

(71) Applicant: Nikkiso Company Limited, Tokyo (JP)

(72) Inventors: Kentaro Kogoshi, Shizuoka (JP); Satoshi Takeuchi, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 107 days.

(21) Appl. No.: 15/149,247

(22) Filed: May 9, 2016

(65) Prior Publication Data

US 2016/0250405 A1 Sep. 1, 2016

Related U.S. Application Data

(63) Continuation of application No. PCT/JP2014/079688, filed on Nov. 10, 2014.

(30) Foreign Application Priority Data

Nov. 11, 2013 (JP) ................................ 2013-232944

(51) Int. Cl.
*A61M 1/36* (2006.01)
*A61M 1/16* (2006.01)

(52) U.S. Cl.
CPC ............ *A61M 1/3643* (2013.01); *A61M 1/16* (2013.01); *A61M 1/3644* (2014.02); *A61M 1/3649* (2014.02); *A61M 1/3652* (2014.02)

(58) Field of Classification Search
CPC .... A61M 1/16; A61M 1/3643; A61M 1/3644; A61M 1/3649; A61M 1/3652
USPC .................................................... 210/321.72
See application file for complete search history.

(56) References Cited

U.S. PATENT DOCUMENTS 6,044,691 A 4/2000 Kenley et al.
9,872,951 B2 1/2018 Furuhashi et al.
2006/0079826 A1 4/2006 Beden et al.
2009/0312686 A1 12/2009 Sakamoto et al.
(Continued)

FOREIGN PATENT DOCUMENTS

EP 2361643 A1 8/2011
EP 2535067 A1 12/2012
(Continued)

OTHER PUBLICATIONS

Extended European Search Report dated May 22, 2017 for Application No. 14860814.4.

(Continued)

*Primary Examiner* — Dirk R Bass
(74) *Attorney, Agent, or Firm* — The Dobrusin Law Firm, PC

(57) ABSTRACT

There are provided a blood purification apparatus and a priming method thereof which can reliably perform air bubble purging of a blood purification device while workability is maintained during priming. During the priming, an air purging step is performed by causing a blood pump to perform reverse rotation, and electromagnetic valves and are brought into an opened state so as to open the overflow line (L) and a priming solution supply line and so as to discharge a priming solution from an overflow line while supplying a dialysate functioning as the priming solution from the priming solution supply line.

10 Claims, 14 Drawing Sheets

(56) References Cited

U.S. PATENT DOCUMENTS

| | | | |
|---|---|---|---|
| 2010/0168640 | A1 | 7/2010 | Kopperschmidt et al. |
| 2010/0274172 | A1 | 10/2010 | Guenther et al. |
| 2011/0213289 | A1* | 9/2011 | Toyoda .............. A61M 1/3643 604/6.09 |
| 2012/0000547 | A1 | 1/2012 | Gronau et al. |
| 2013/0035626 | A1 | 2/2013 | Suzuki |
| 2015/0021244 | A1 | 1/2015 | Furuhashi et al. |
| 2015/0151036 | A1 | 6/2015 | Furuhashi et al. |

FOREIGN PATENT DOCUMENTS

| | | | |
|---|---|---|---|
| EP | 2883558 | A1 | 6/2015 |
| JP | S60-153138 | | 10/1985 |
| JP | 2004-016619 | A | 1/2004 |
| JP | 2005-253555 | A | 4/2006 |
| JP | 2006-280775 | A | 10/2006 |
| JP | 2007-007435 | A | 1/2007 |
| JP | 2007-167108 | A | 7/2007 |
| JP | 2007-282737 | A | 6/2008 |
| JP | 2009-112651 | A | 5/2009 |
| JP | 2010-000161 | A | 5/2009 |
| JP | 2009-131412 | A | 6/2009 |
| JP | 2010-273784 | A | 12/2009 |
| JP | 2010-269050 | A | 12/2010 |
| JP | 2010-273693 | A | 12/2010 |
| JP | 2011-161059 | A | 8/2011 |
| JP | 2012-095843 | A | 5/2012 |
| JP | 2012/139405 | A | 7/2012 |
| JP | 2012-192099 | A | 10/2012 |
| WO | 2005/118485 | A | 12/2005 |
| WO | 2011/099521 | A1 | 5/2011 |
| WO | 2014/024972 | A1 | 2/2014 |
| WO | 2015/068833 | A1 | 5/2015 |

OTHER PUBLICATIONS

Extended European Search Report, Application No. 13768746.3 dated Oct. 16, 2015.

International Search Report for Application No. PCT-JP2014-079688, dated Jan. 27, 2015.

Potentially related co-pending Patent Application published as 2015/0021244.

Potentially related co-pending Patent Application published as 2015/0151036.

Potentially related co-pending Patent Application published as 2013/0035626.

Japanese Office Action, Application No. 2014-529557; dated May 10, 2017.

Supplementary European Search Report dated Mar. 16, 2016, for Application No. PCT/JP2013071511.

* cited by examiner

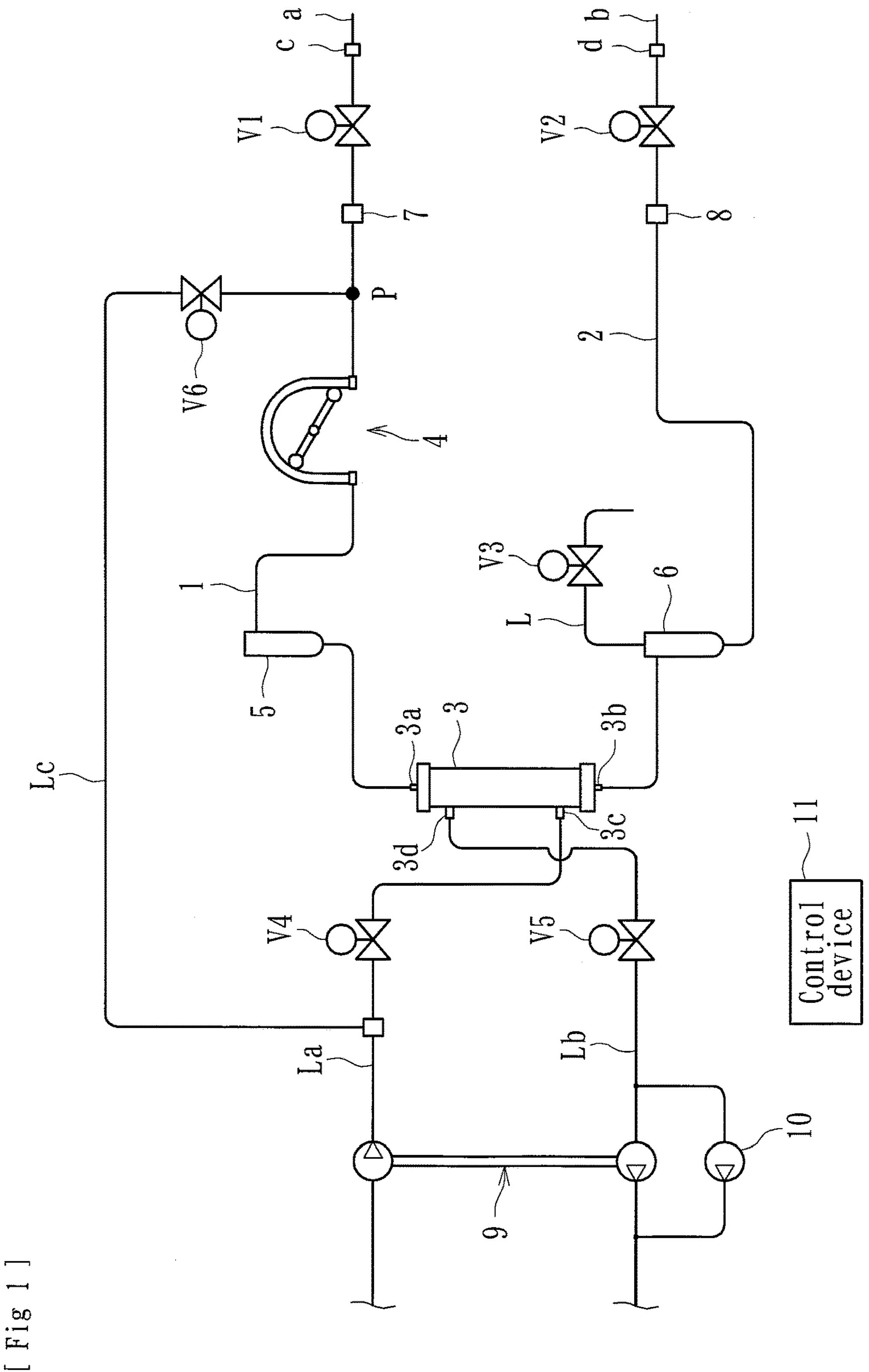
[ Fig 1 ]
c a
d b
V1
V2
7
8
P
2
V6
4
1
V3
6
L
5
3a
3
3b
Lc
3d
3c
V4
V5
11
Control device
La
Lb
10
9

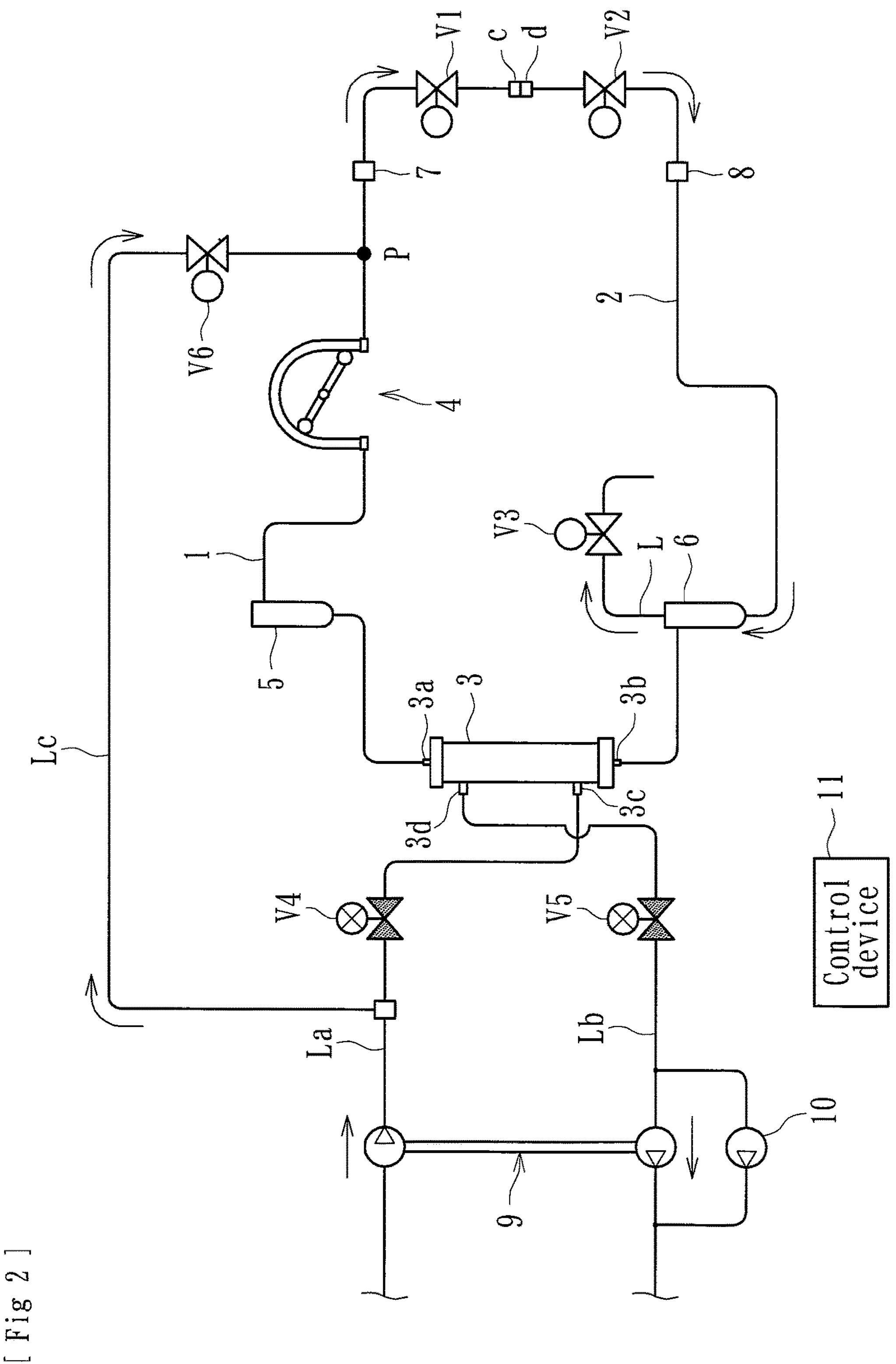
[ Fig 2 ]
V1
c
d
V2
7
8
P
V6
4
2
1
V3
L
6
5
3a
3
3b
Lc
3d
3c
11
V4
V5
Control device
La
Lb
10
9

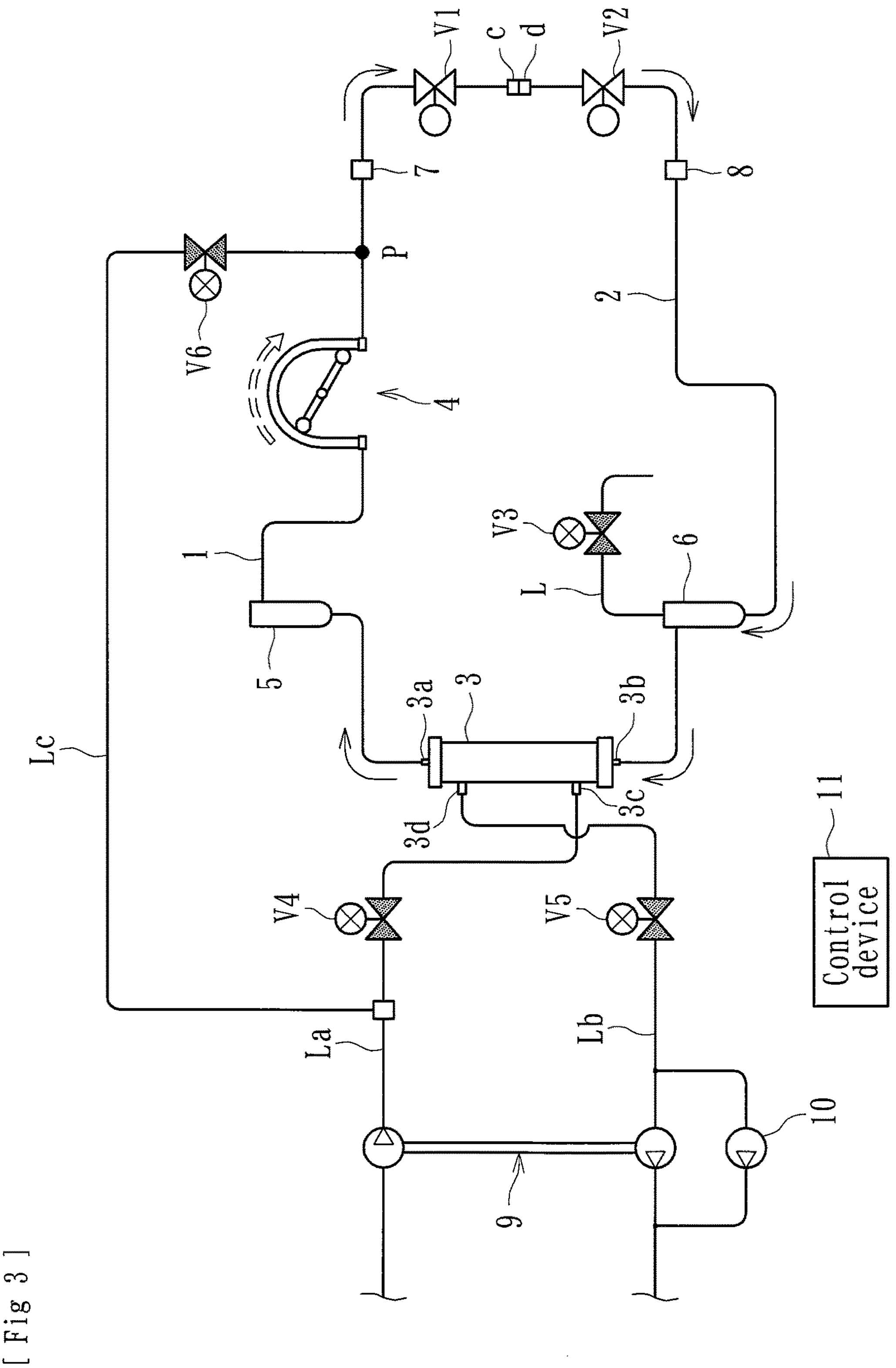
[ Fig 3 ]
V1
c
d
V2
7
8
P
V6
4
2
V3
6
1
L
5
3a
3
3b
Lc
3d
3c
11
V4
V5
Control device
La
Lb
10
9

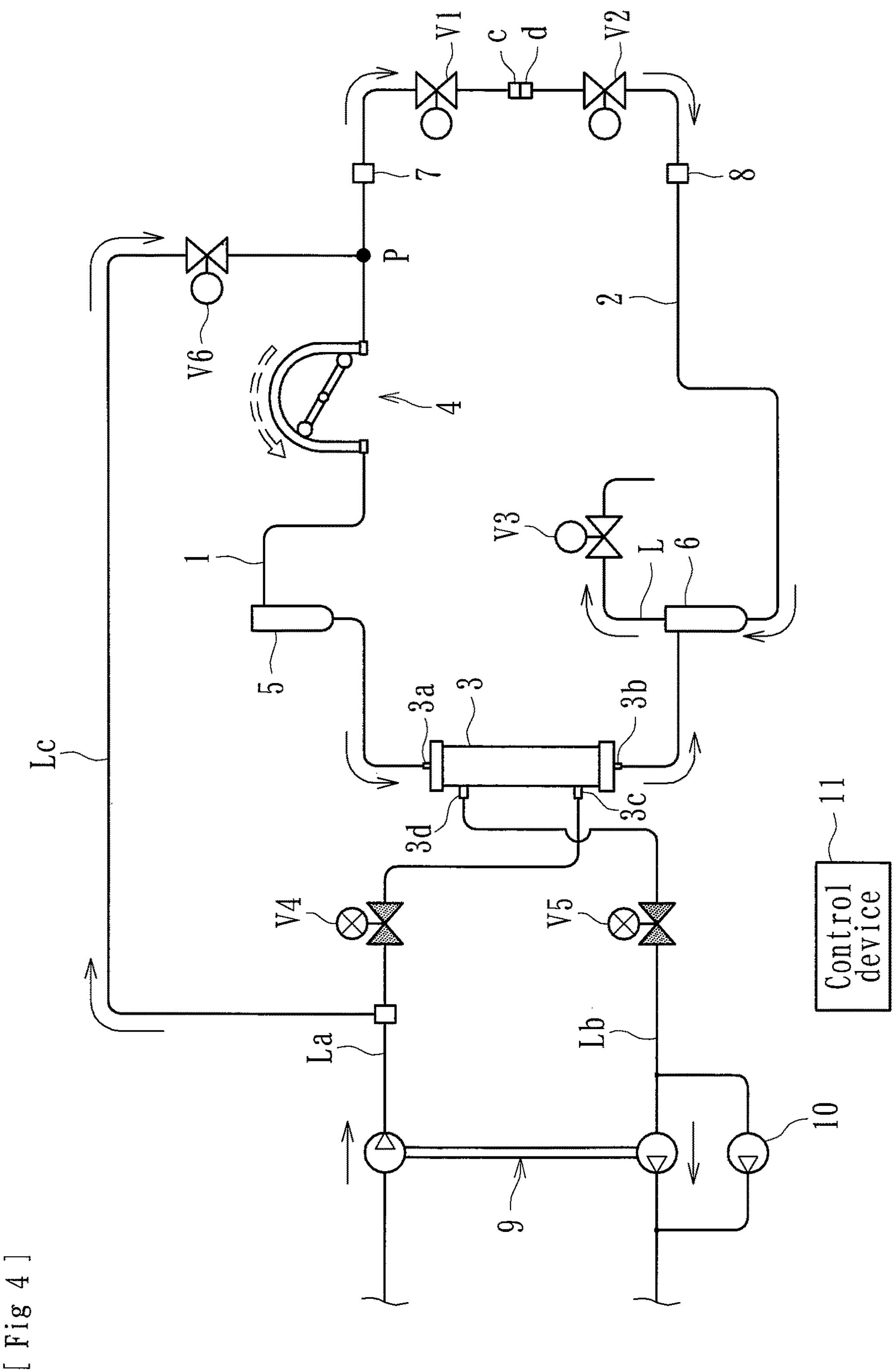
[ Fig 4 ]

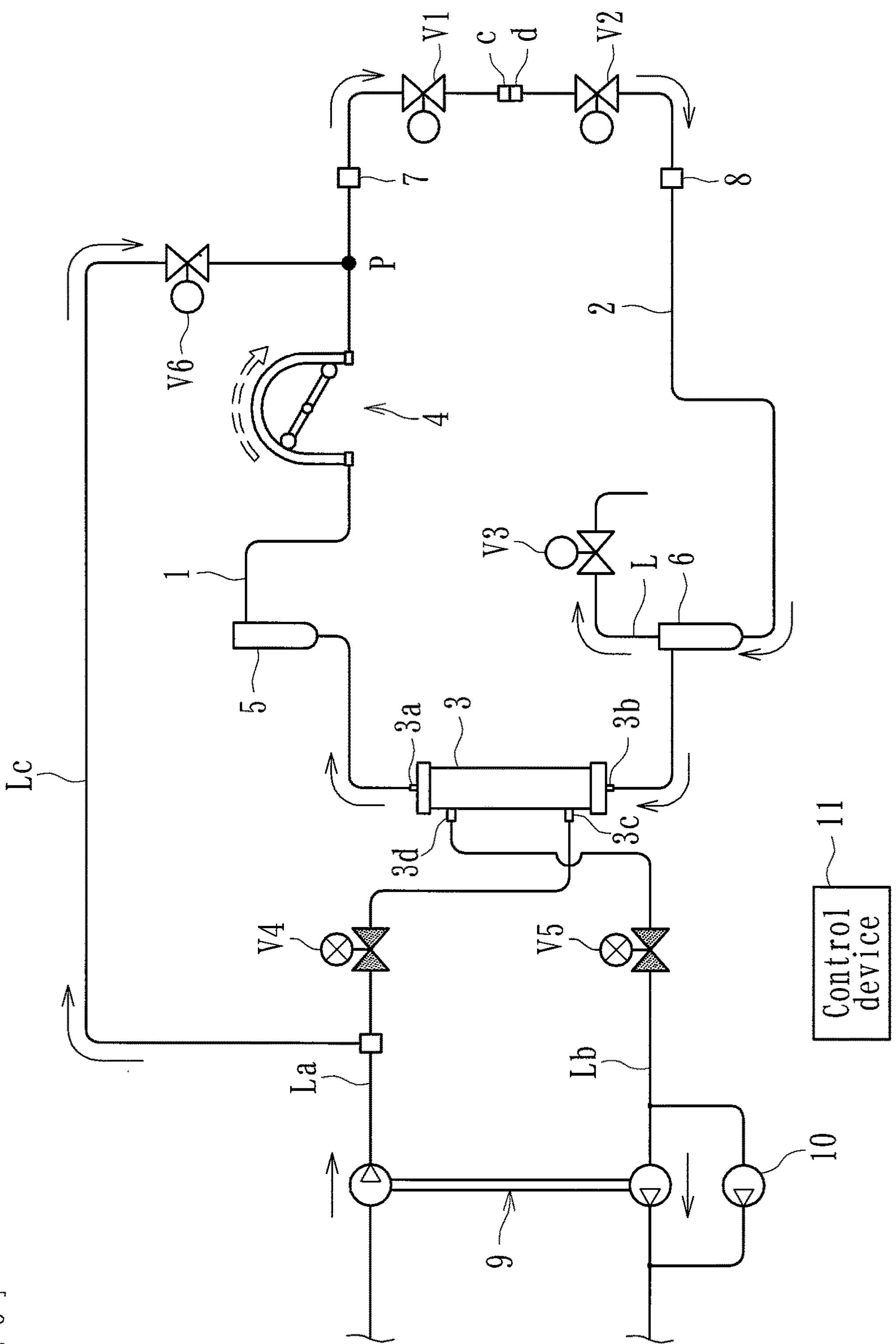
[ Fig 5 ]

[ Fig 6 ]
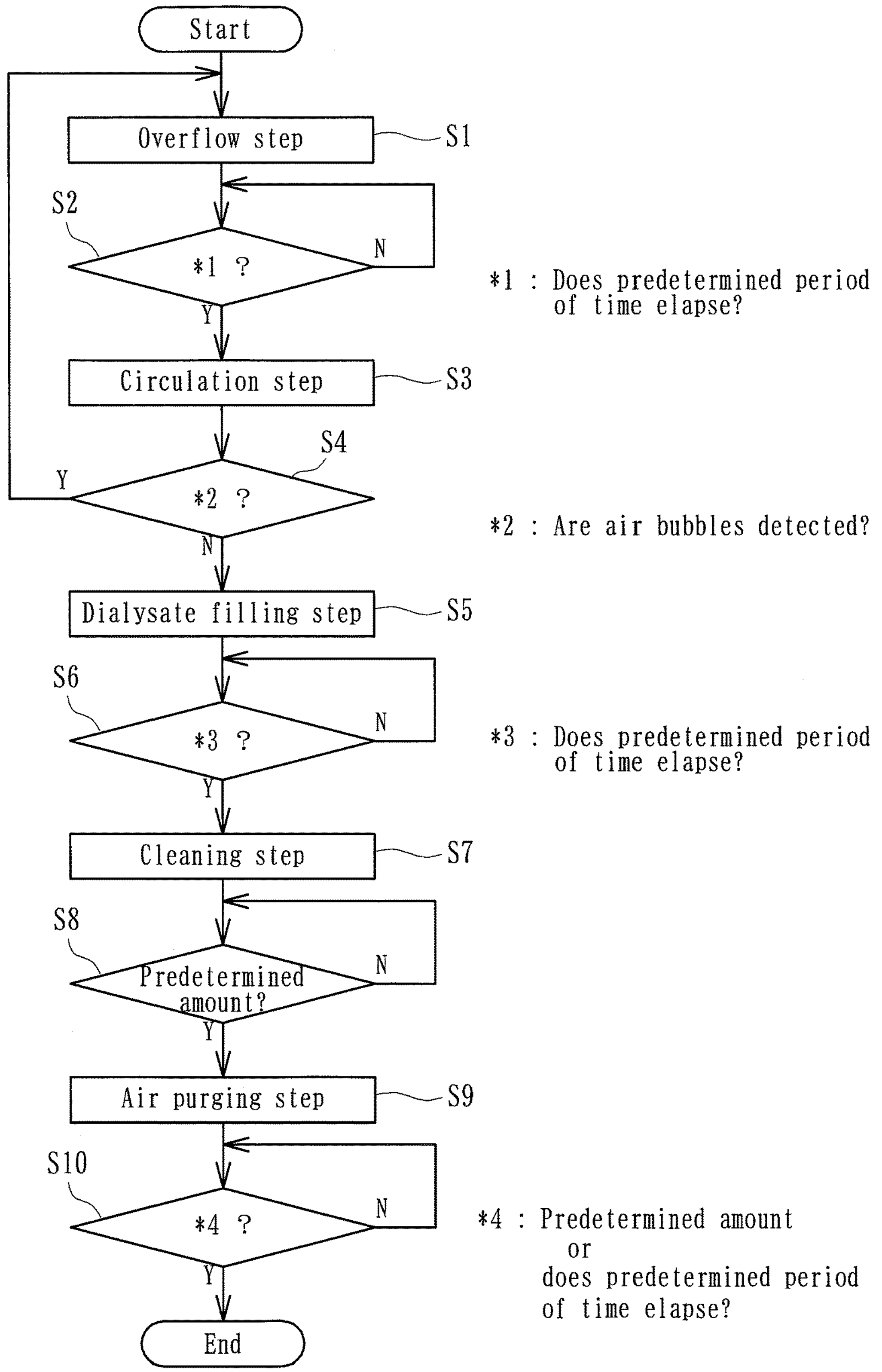

[ Fig 7 ]
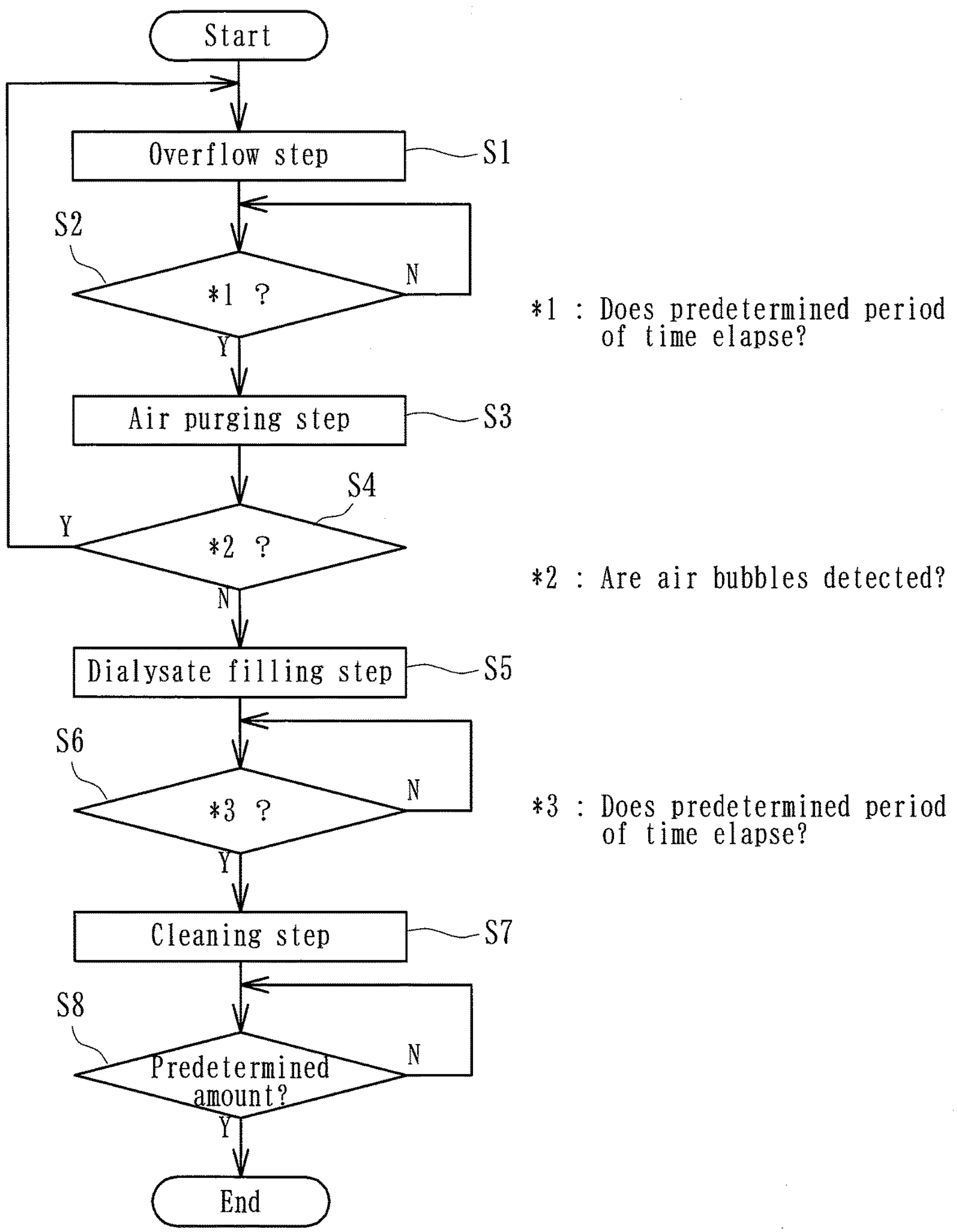

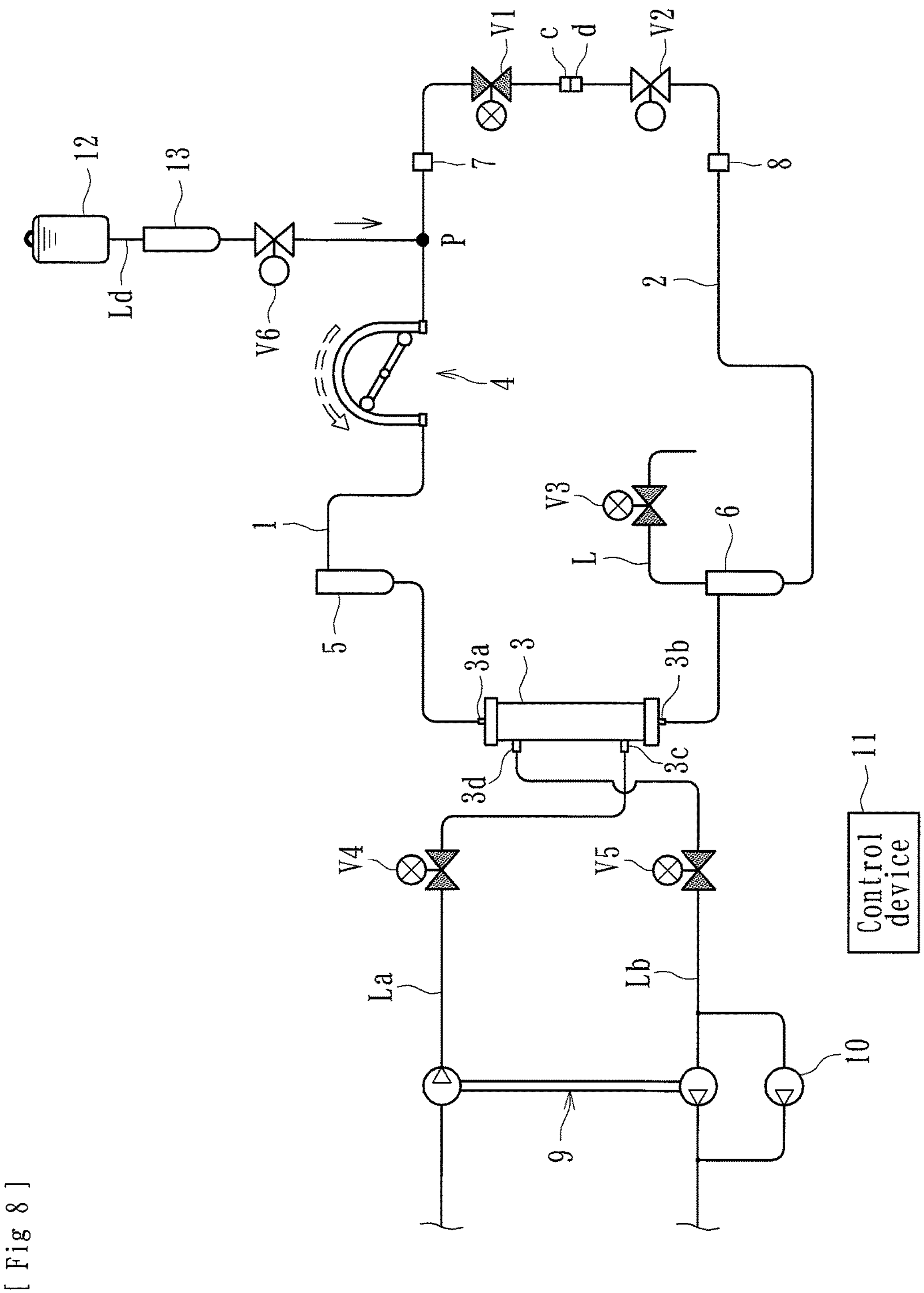
[ Fig 8 ]

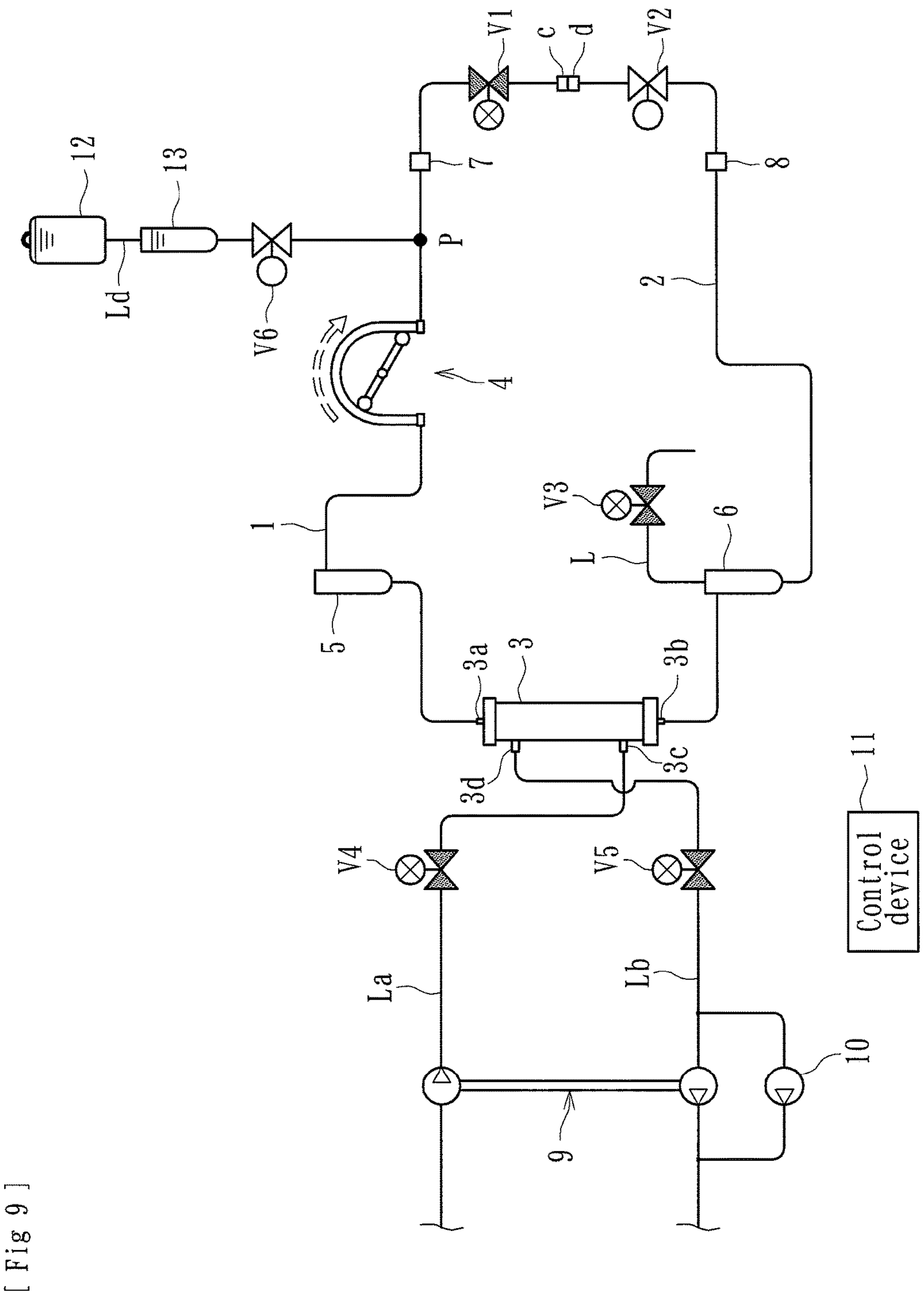
[ Fig 9 ]

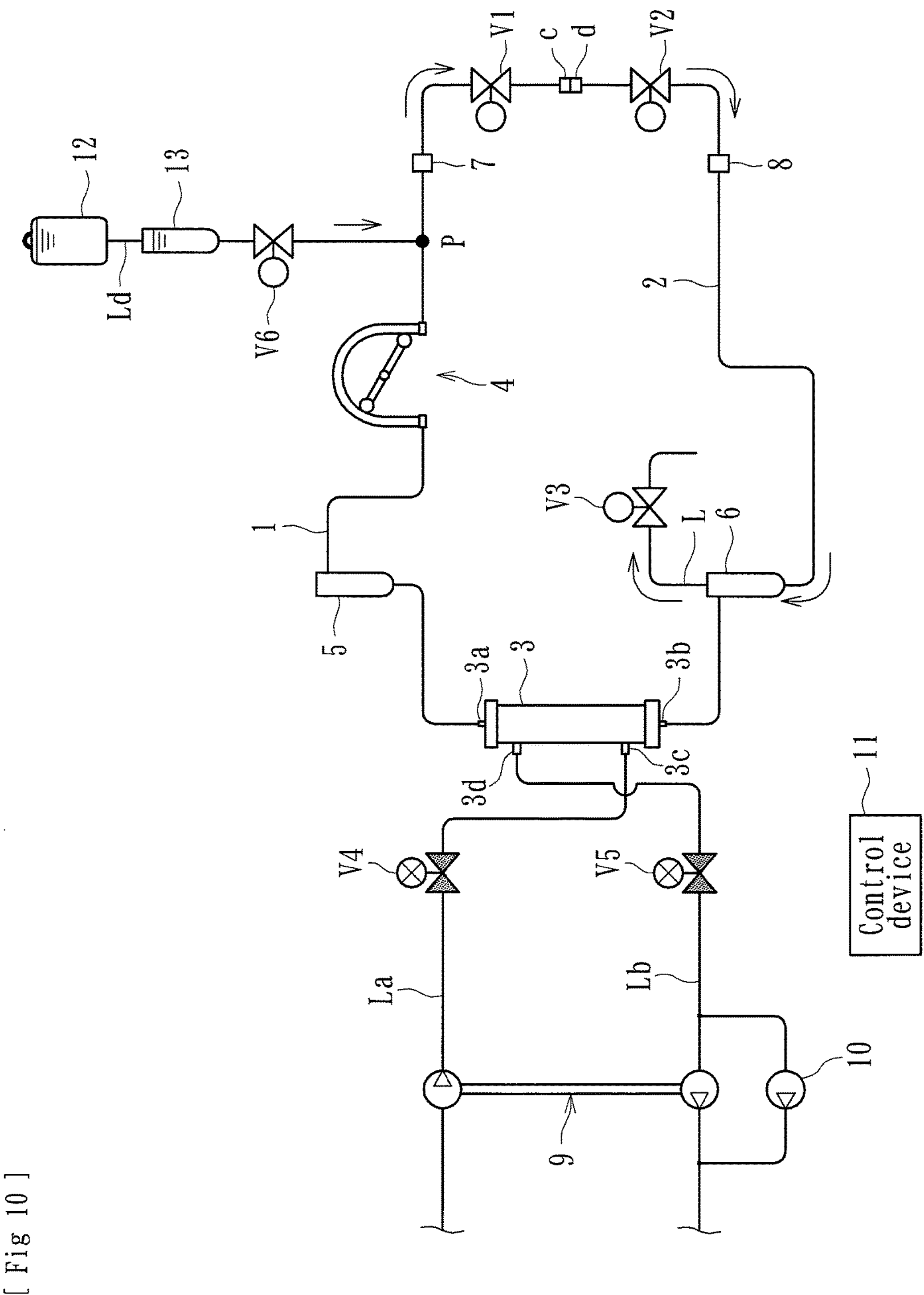
[ Fig 10 ]
12
13
Ld
V6
P
V1
c
d
V2
7
8
2
1
4
V3
L
6
5
3a
3
3b
3d
3c
V4
V5
La
Lb
9
10
11
Control device

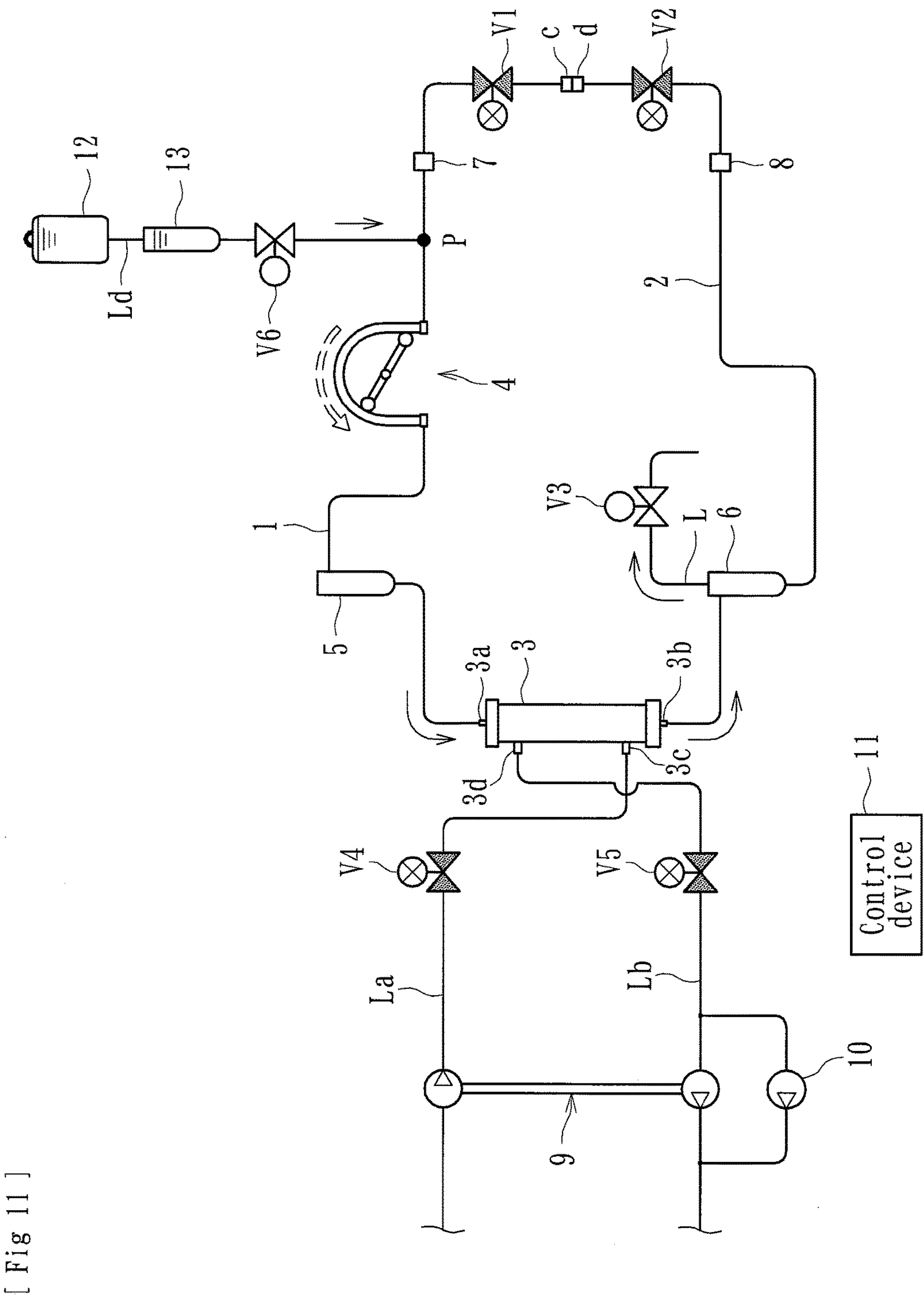
[ Fig 11 ]

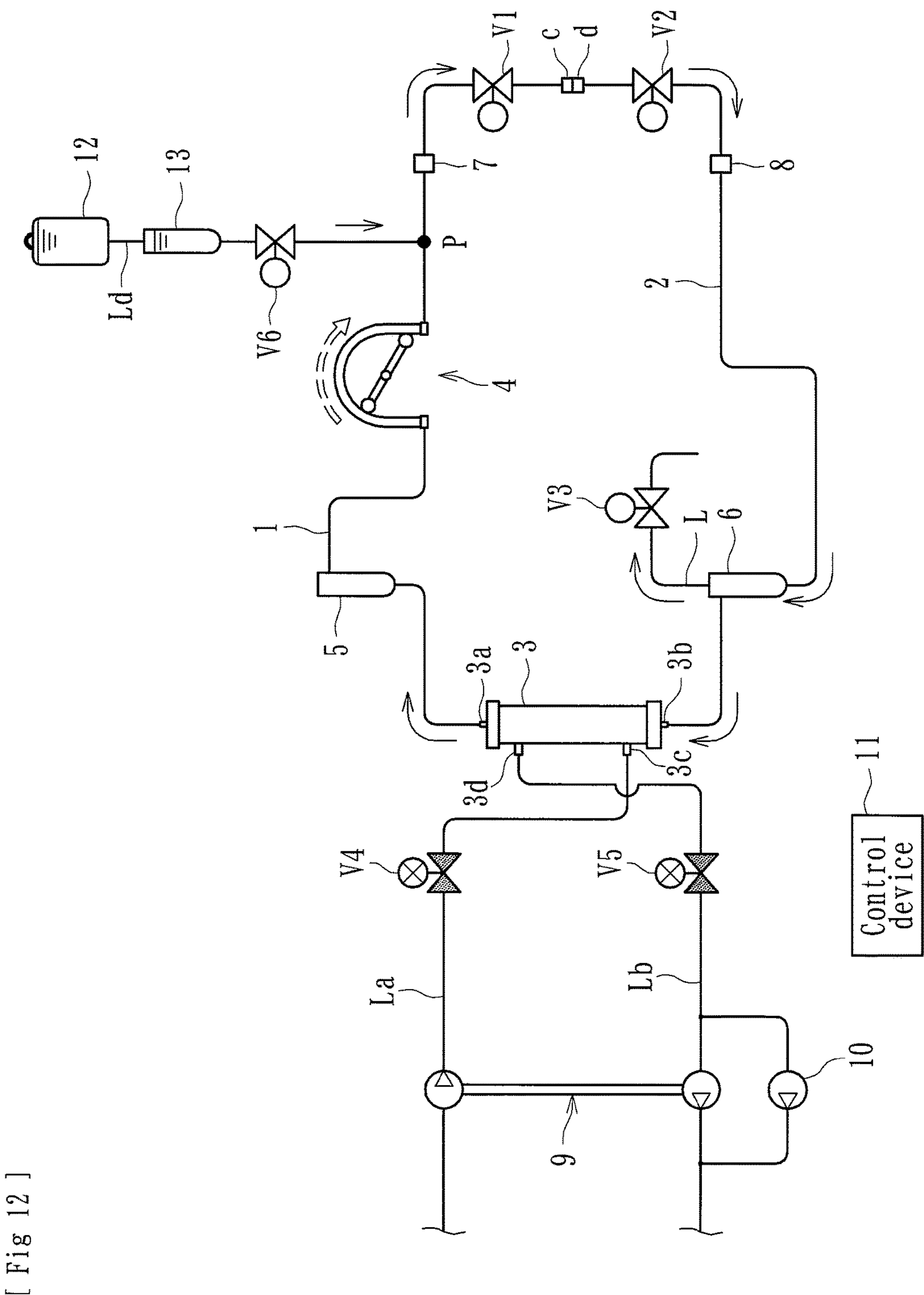
[ Fig 12 ]

[ Fig 13 ]
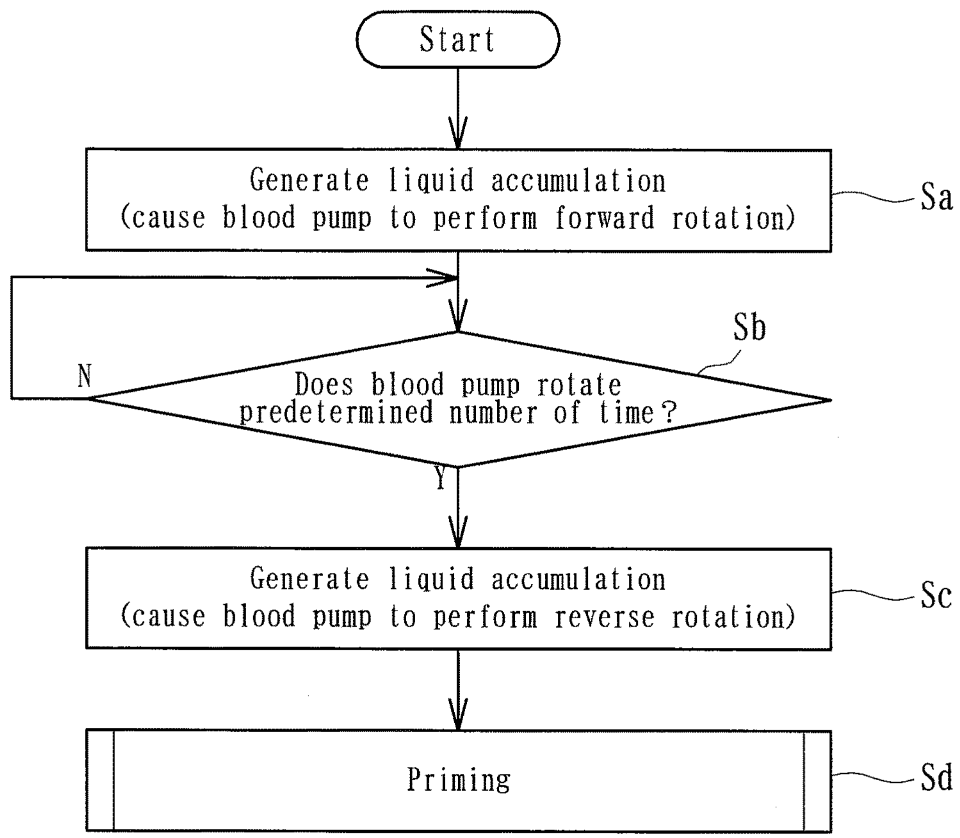

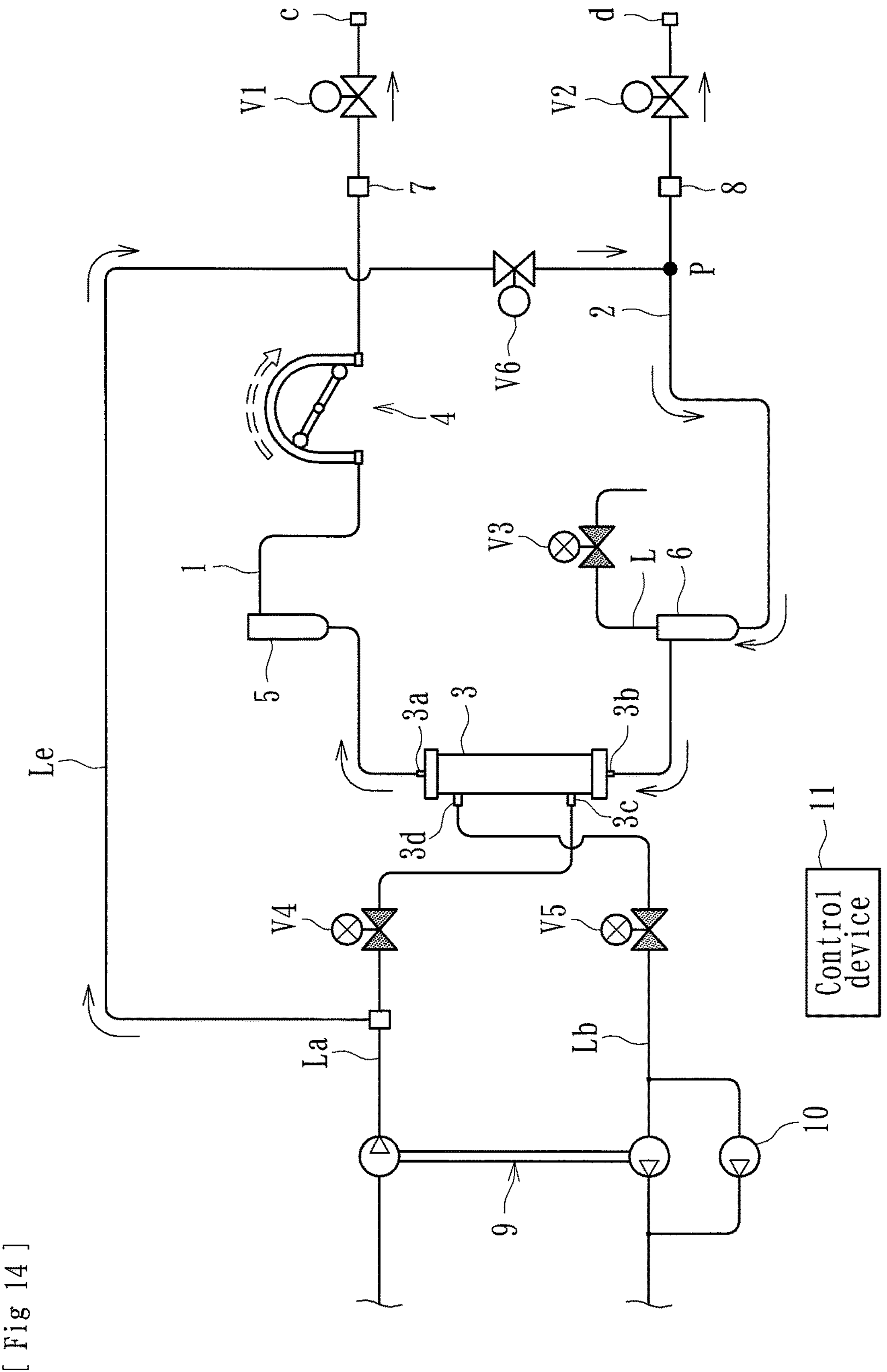
[ Fig 14 ]

BLOOD PURIFICATION APPARATUS AND PRIMING METHOD THEREOF

FIELD

The present invention relates to a blood purification apparatus and a priming method thereof which are used in order to extracorporeally circulate and purify blood of a patient in dialysis treatment using a dialyzer.

BACKGROUND

In general, during dialysis treatment, a blood circuit is used which extracorporeally circulates blood collected from a patient and which returns the blood into the internal body of the patient. For example, the blood circuit is mainly configured to have an arterial blood circuit and a venous blood circuit which can be connected to a dialyzer (blood purification device) including a hollow fiber membrane. An arterial puncture needle and a venous puncture needle are attached to each distal end of the arterial blood circuit and the venous blood circuit. The respective needles are adapted to puncture the patient so as to perform extracorporeal circulation of the blood for the dialysis treatment.

Out of these blood circuits, a peristaltic blood pump is arranged in the arterial blood circuit, and the blood pump is rotated so as to feed the blood to the dialyzer side from the internal body of the patient. In contrast, an arterial drip chamber and a venous drip chamber are respectively connected to the arterial blood circuit and the venous blood circuit. The blood is adapted to return to the internal body of the patient after bubbles are removed.

In addition, a priming solution supply line for supplying a priming solution into the blood circuit is connected to an upstream side (that is, the arterial puncture needle side) further from the blood pump in the arterial blood circuit. Before the dialysis treatment, the priming solution is caused to flow into the blood circuit or configuration elements such as the blood circuit, the blood flow route of the dialyzer and the drip chamber connected to the blood circuit so as to be filled with the priming solution. According to this configuration, priming can be performed.

Air bubbles inside the blood flow route move upward when the priming is performed on the blood flow route of the dialyzer by using the priming solution. Accordingly, it is necessary to perform air bubble purging by causing a blood outlet to face upward and drawing out the air bubbles to the venous blood circuit side. In contrast, in a case where the priming is performed on a dialysis flow route by using a dialysate in this state, the blood and the dialysate flow in opposite directions. Accordingly, the dialysate flows from above to below, and flows in a direction opposite to a movement direction of the air bubbles. Therefore, the dialyzer is vertically inverted so that the dialysate flows from below to above. In this manner, more reliable air bubble purging can be performed by ensuring smooth movement of the air bubbles.

However, in a case where the dialyzer is vertically inverted when the priming is performed as described above, there is a problem in that workability becomes poor correspondingly and the priming is less likely to be automated. In order to solve the problem, in the related art, a blood purification apparatus has been proposed. In the blood purification apparatus, an overflow step of supplying the priming solution from the priming solution supply line to the venous air trap chamber via the venous blood circuit and discharging the priming solution from an overflow line by stopping the blood pump and by opening the overflow line and a circulation step of supplying the priming solution from the priming solution supply line to the arterial blood circuit via the venous blood circuit and the dialyzer by causing the blood pump to perform reverse rotation and closing the overflow line are sequentially performed in a state where a blood inlet of the dialyzer faces upward. In the circulation step, a venous air bubble detection device detects air bubbles so that the step proceeds to the overflow step (refer to PTL 1).

CITATION LIST

Patent Literature

PTL 1: Japanese Unexamined Patent Application Publication No. 2010-273693

SUMMARY

According to the above-described blood purification apparatus in the related art, a priming step can be performed while a state where the blood inlet of the dialyzer faces upward is maintained. However, for example, in a case where the above-described blood purification apparatus is applied to an apparatus in which the arterial air trap chamber is connected to the arterial blood circuit, the air bubbles accumulated near the blood inlet of the dialyzer during the circulation step flow into the arterial air trap chamber side, thereby causing a possibility that a liquid level of the arterial air trap chamber may be excessively lowered. In this case, before the step proceeds to a blood treatment step, it becomes necessary to carry out work for maintaining a proper liquid level by forcibly purging the air bubbles present inside the arterial air trap chamber. Consequently, there is a problem in that workability of the priming becomes poor.

The present teachings are made in view of these circumstances, and aims to provide a blood purification apparatus and a priming method thereof which can reliably perform air bubble purging of a blood purification device while workability is maintained during priming.

According to the present teachings, there is provided a blood purification apparatus including a blood circuit that includes an arterial blood circuit and a venous blood circuit, and that can extracorporeally circulate blood of a patient from a distal end of the arterial blood circuit to a distal end of the venous blood circuit, a blood purification device that purifies the blood flowing in the blood circuit by being interposed between the arterial blood circuit and the venous blood circuit of the blood circuit, that has a blood flow route through which the blood of the patient flows via a blood purification membrane for purifying the blood and a dialysate flow route through which a dialysate flows, and that has a blood inlet which can introduce the blood to the blood flow route, a blood outlet which can draw out the blood from the blood flow route, a dialysate inlet which can introduce the dialysate to the dialysate flow route, and a dialysate outlet which can discharge the dialysate from the dialysate flow route, a blood pump that is arranged in the arterial blood circuit, and that is capable of forward rotation which rotates in a direction of circulating the blood during blood purification treatment and reverse rotation which rotates in a direction opposite to the direction of circulating the blood during the blood purification treatment, a priming solution supply line that is connected to the blood circuit, and that can supply a priming solution into the blood circuit, a priming solution discharge unit that can cause the priming solution supplied by the priming solution supply line to overflow from the blood circuit so as to be discharged outward, a first valve device that can selectively close or open the priming solution supply line, a second valve device that can selectively close or open the priming solution discharge unit, and a control device that can control the blood pump, the first valve device, and the second valve device. Priming is performed in a state where the blood inlet of the blood purification device faces upward. During the priming, the control device performs an air purging step of causing the blood pump to perform the reverse rotation, and opening the priming solution discharge unit and the priming solution supply line so as to discharge the priming solution from the priming solution discharge unit, while supplying the priming solution from the priming solution supply line.

According to the present teachings, in the blood purification apparatus described herein, an arterial air trap chamber is connected between the blood pump and the blood purification device in the arterial blood circuit.

According to the present teachings, in the blood purification apparatus described herein, a venous air trap chamber is connected to the venous blood circuit, and the priming solution discharge unit includes an overflow line which extends from an upper portion of the venous air trap chamber.

According to the present teachings, there is provided a priming method of a blood purification apparatus including a blood circuit that includes an arterial blood circuit and a venous blood circuit, and that can extracorporeally circulate blood of a patient from a distal end of the arterial blood circuit to a distal end of the venous blood circuit, a blood purification device that purifies the blood flowing in the blood circuit by being interposed between the arterial blood circuit and the venous blood circuit of the blood circuit, that has a blood flow route through which the blood of the patient flows via a blood purification membrane for purifying the blood and a dialysate flow route through which a dialysate flows, and that has a blood inlet which can introduce the blood to the blood flow route, a blood outlet which can draw out the blood from the blood flow route, a dialysate inlet which can introduce the dialysate to the dialysate flow route, and a dialysate outlet which can discharge the dialysate from the dialysate flow route, a blood pump that is arranged in the arterial blood circuit, and that is capable of forward rotation which rotates in a direction of circulating the blood during blood purification treatment and reverse rotation which rotates in a direction opposite to the direction of circulating the blood during the blood purification treatment, a priming solution supply line that is connected to the blood circuit, and that can supply a priming solution into the blood circuit, a priming solution discharge unit that can cause the priming solution supplied by the priming solution supply line to overflow from the blood circuit so as to be discharged outward, a first valve device that can selectively close or open the priming solution supply line, and a second valve device that can selectively close or open the priming solution discharge unit. Priming is performed in a state where the blood inlet of the blood purification device faces upward. During the priming, an air purging step is performed by causing the blood pump to perform the reverse rotation, and opening the priming solution discharge unit and the priming solution supply line so as to discharge the priming solution from the priming solution discharge unit while supplying the priming solution from the priming solution supply line.

According to the present teachings, in the priming method of the blood purification apparatus described herein, an arterial air trap chamber is connected between the blood pump and the blood purification device in the arterial blood circuit.

According to the present teachings, in the priming method of the blood purification apparatus described herein, a venous air trap chamber is connected to the venous blood circuit, and the priming solution discharge unit includes an overflow line which extends from an upper portion of the venous air trap chamber.

According to the present teachings, during the priming, the air purging step is performed by causing the blood pump to perform the reverse rotation, and opening the priming solution discharge unit and the priming solution supply line so as to discharge the priming solution from the priming solution discharge unit while supplying the priming solution from the priming solution supply line. Therefore, the air bubble purging of a blood purification device can be reliably performed while workability is maintained during the priming.

According to the present teachings, the arterial air trap chamber is connected between the blood pump and the blood purification device in the arterial blood circuit. Accordingly, air bubbles accumulated near the blood inlet of the blood purification device can be accommodated in the arterial air trap chamber, and air bubbles excessively flowing into the arterial air trap chamber can be discharged together with the priming solution from the priming solution discharge unit.

According to the present teachings, the venous air trap chamber is connected to the venous blood circuit, and the priming solution discharge unit includes the overflow line which extends from the upper portion of the venous air trap chamber. Accordingly, the priming solution supplied from the priming solution supply line can be discharged outward by utilizing the venous air trap chamber and the overflow line which are generally disposed in the blood circuit.

BRIEF DESCRIPTION OF DRAWINGS

FIG. 1 is a schematic view illustrating a blood purification apparatus (state where a puncture needle is attached) according to a first embodiment of the present invention.

FIG. 2 is a schematic view illustrating a state (overflow step) during priming in the blood purification apparatus.

FIG. 3 is a schematic view illustrating a state (circulation step) during the priming in the blood purification apparatus.

FIG. 4 is a schematic view illustrating a state (cleaning step) during the priming in the blood purification apparatus.

FIG. 5 is a schematic view illustrating a state (air purging step) during the priming in the blood purification apparatus.

FIG. 6 is a flowchart illustrating control content during the priming in the blood purification apparatus.

FIG. 7 is a flowchart illustrating control content during priming in a blood purification apparatus according to a second embodiment of the present invention.

FIG. 8 is a schematic view illustrating a blood purification apparatus (state where a blood pump is caused to perform forward rotation during a liquid accumulation generating step before priming) according to a third embodiment of the present invention.

FIG. 9 is a schematic view illustrating the blood purification apparatus (state where the blood pump is caused to perform reverse rotation during the liquid accumulation generating step before the priming)

FIG. 10 is a schematic view illustrating a state (cleaning step) during the priming in the blood purification apparatus.

FIG. 11 is a schematic view illustrating a state (cleaning step) during the priming in the blood purification apparatus.

FIG. 12 is a schematic view illustrating a state (air purging step) during the priming in the blood purification apparatus.

FIG. 13 is a flowchart illustrating control content of the liquid accumulation generating step in the blood purification apparatus according to the embodiment.

FIG. 14 is a schematic view illustrating a blood purification apparatus (state where a blood pump is caused to perform reverse rotation during a liquid accumulation generating step before priming) according to a fourth embodiment of the present invention.

DESCRIPTION OF EMBODIMENTS

Hereinafter, embodiments of the present invention will be described in detail with reference to the drawings.

A blood purification apparatus according to a first embodiment includes a dialysis apparatus for performing dialysis treatment. As illustrated in FIG. 1, the blood purification apparatus is mainly configured to include a blood circuit that has an arterial blood circuit 1 and a venous blood circuit 2, a dialyzer 3 (blood purification device) that is interposed between the arterial blood circuit 1 and the venous blood circuit 2 so as to purify blood flowing in the blood circuit, a peristaltic blood pump 4 that is arranged in the arterial blood circuit 1, an arterial air trap chamber 5 that is connected to the arterial blood circuit 1, a venous air trap chamber 6 that is connected to the venous blood circuit 2, a priming solution supply line Lc, an overflow line L functioning as a priming solution discharge unit, an electromagnetic valve V6 functioning as a first valve device, an electromagnetic valve V3 functioning as a second valve device, and a control device 11.

In the arterial blood circuit 1, an arterial puncture needle a is connected to a distal end thereof via a connector c, and the peristaltic blood pump 4 is arranged in an intermediate portion of the arterial blood circuit 1. The blood pump 4 is capable of forward rotation (rotation to the left in FIG. 1) which rotates in a direction of circulating the blood during blood purification treatment and reverse rotation (rotation to the right in FIG. 1) which rotates in a direction opposite to the direction of circulating the blood during the blood purification treatment. In addition, the arterial air trap chamber 5 is connected between the blood pump 4 and the dialyzer 3 in the arterial blood circuit 1 so as to remove bubbles from a liquid flowing in the arterial blood circuit 1.

On the other hand, in the venous blood circuit 2, a venous puncture needle b is connected to a distal end thereof via a connector d, and the venous air trap chamber 6 is connected to an intermediate portion of the venous blood circuit 2 so that bubbles can be removed from a liquid flowing in the venous blood circuit 2. The overflow line L (priming solution discharge unit) extends from an upper portion (air layer side) of the venous air trap chamber 6, and is configured so that a liquid overflowing from the air trap chamber 6 is discharged outward. In addition, the electromagnetic valve V3 functioning as the second valve device which can selectively close or open a flow route of the overflow line L is arranged in the overflow line L.

Then, in a state where the arterial puncture needle a and the venous puncture needle b puncture a patient, if the blood pump 4 is caused to perform the forward rotation, bubbles in blood of the patient are removed by the arterial air trap chamber 5, and the blood reaches the dialyzer 3 after passing through the arterial blood circuit 1. Thereafter, the blood is purified by the dialyzer 3, the bubbles are removed from the blood by the venous air trap chamber 6, and the blood returns to the internal body of the patient after passing through the venous blood circuit 2. In this manner, the blood of the patient is purified by the dialyzer 3 while the blood is extracorporeally circulated from a distal end of the arterial blood circuit 1 to a distal end of the venous blood circuit 2 in the blood circuit.

A housing unit of the dialyzer 3 has a blood inlet 3*a* (blood inlet port), a blood outlet 3*b* (blood outlet port), a dialysate inlet 3*c* (dialysate flow route entrance: dialysate inlet port), and a dialysate outlet 3*d* (dialysate flow route exit: dialysate outlet port). In this configuration, a proximal end of the arterial blood circuit 1 is connected to the blood inlet 3*a*, and a proximal end of the venous blood circuit 2 is connected to the blood outlet 3*b*. In addition, the dialysate inlet 3*c* and the dialysate outlet 3*d* are respectively connected to a dialysate introduction line La and a dialysate discharge line Lb which extend from a dialysis apparatus main body.

Multiple hollow fibers (not illustrated) are accommodated inside the dialyzer 3, and the hollow fibers configure a blood purification membrane for purifying the blood. In this manner, the dialyzer 3 internally has a blood flow route through which the blood of the patient flows via the blood purification membrane (flow route between the blood inlet 3*a* and the blood outlet 3*b*, which is an internal space of the hollow fiber membrane) and a dialysate flow route through which a dialysate flows (flow route between the dialysate inlet 3*c* and the dialysate outlet 3*d*, which is an outer space of the hollow fiber membrane).

That is, the dialyzer 3 has the blood inlet 3*a* which can introduce the blood into the blood flow route, the blood outlet 3*b* which can draw out the blood from the blood flow route, the dialysate inlet 3*c* which can introduce the dialysate into the dialysate flow route, and the dialysate outlet 3*d* which can draw out the dialysate from the dialysate flow route. The dialyzer 3 is configured so that the blood flowing from the blood inlet 3*a* toward the blood outlet 3*b* and the dialysate flowing from the dialysate inlet 3*c* toward the dialysate outlet 3*d* flow in opposite directions. In addition, many minute apertures (pores) penetrating an outer peripheral surface and an inner peripheral surface of the hollow fibers are formed in the hollow fibers configuring the blood purification membrane, thereby forming the hollow fiber membrane. In this configuration, impurities or the like contained in the blood can permeate into the dialysate via the membrane.

The duplex pump 9 is arranged across the dialysate introduction line La and the dialysate discharge line Lb inside the dialysis apparatus main body. An ultrafiltration pump 10 for removing water from the blood of the patient which flows in the dialyzer 3 is arranged in the dialysis apparatus main body. In the dialysate introduction line La, one end thereof is connected to the dialyzer 3 (dialyzer inlet 3*c*), and the other end is connected to a dialysate supply device (not illustrated) which prepares the dialysate having a predetermined concentration. In addition, in the dialysate discharge line Lb, one end thereof is connected to the dialyzer 3 (dialysate outlet 3*d*), and the other end is connected to a liquid discharge device (not illustrated). The dialysate supplied from the dialysate supply device reaches the dialyzer 3 after passing through the dialysate introduction line La, and is circulated in the dialysate flow route. Thereafter, the dialysate is fed to the liquid discharge device after passing through the dialysate discharge line Lb.

An electromagnetic valve V4 which can close and open a flow route of the dialysate introduction line La is connected to an intermediate portion (between the duplex pump 9 and the dialyzer 3) of the dialysate introduction line La, and an electromagnetic valve V5 which can selectively close and open a flow route of the dialysate discharge line Lb is connected to an intermediate portion (between the duplex pump 9 and the dialyzer 3) of the dialysate discharge line Lb. In addition, electromagnetic valves V1 and V2 which can selectively close and open a flow route thereof are respectively connected to a distal end side (near the connector c) of the arterial blood circuit 1 and a distal side (near the connector d) of the venous blood circuit 2. Furthermore, an arterial air bubble detection device 7 which can detect air bubbles in the liquid flowing in the adjacent area is arranged on the distal side of the arterial blood circuit 1, and a venous air bubble detection device 8 which can detect air bubbles in the liquid flowing in the adjacent area is arranged on the distal side of the venous blood circuit 2.

A distal end of the priming solution supply line Lc is connected to the blood circuit (connection portion P between the electromagnetic valve V1 and the blood pump 4 in the arterial blood circuit 1) so that a priming solution (dialysate) can be supplied into the blood circuit. According to the present embodiment, a proximal end thereof is connected between the duplex pump 9 and the electromagnetic valve V4 in the dialysate introduction line La. In addition, an electromagnetic valve V6 functioning as a first valve device which can selectively close and open a flow route thereof is arranged in an intermediate portion of the priming solution supply line Lc.

The electromagnetic valve V6 is brought into an open state while the electromagnetic valve V4 is brought into a closed state, and the duplex pump 9 is rotated. In this configuration, the dialysate of the dialysate introduction line La is supplied to the blood circuit via the priming solution supply line Lc. As described above, according to the present embodiment, the dialysate flowing in the dialysate introduction line La is supplied to the blood circuit (arterial blood circuit 1) as the priming solution.

The control device 11 is electrically connected to various configuration components including the blood pump 4, the duplex pump 9, and the electromagnetic valves V1 to V6 in the blood purification apparatus, and can control the configuration components. For example, the control device 11 includes a microcomputer or the like arranged in the dialysis apparatus main body. A configuration is adopted in which the control device 11 can operate any desired configuration component during priming prior to treatment, blood purification treatment, or blood returning after treatment. The control device 11 may control the configuration component only during the priming.

During the priming prior to treatment (work for filling the blood circuit or the blood flow route with the priming solution in advance by circulating the priming solution so as to clean the blood circuit or the blood flow route of the dialyzer 3), the distal end of the arterial blood circuit 1 and the distal end of the venous blood circuit 2 can be connected to and communicate with each other (specifically, mutual flow routes can communicate with each other by connecting the connector c and the connector d).

Here, during the priming, as illustrated in FIG. 5, the blood purification apparatus according to the present embodiment causes the control device 11 to control an air purging step of causing the blood pump 4 to perform reverse rotation, the electromagnetic valves V3 and V6 are brought into an open state, and the overflow line L (priming solution discharge unit) and the priming solution supply line Lc are opened so as to discharge the priming solution (dialysate) from the overflow line L, while supplying the priming solution (dialysate) from the priming solution supply line Lc.

Hereinafter, the priming performed by the blood purification apparatus according to the present embodiment will be described with reference to a flowchart in FIG. 6.

During the priming, as illustrated in FIG. 2, the blood inlet 3*a* of the dialyzer 3 is brought into a state of facing upward (fixed by a fixing device (not illustrated)), and the connector c and the connector d are connected to each other so that the mutual flow routes communicate with each other. Thereafter, the control device 11 brings the electromagnetic valves V1, V2, V3, and V6 into an open state, and brings the electromagnetic valves V4 and V5 into a closed state. The duplex pump 9 is rotated so as to perform an overflow step S1.

In the overflow step S1, the blood pump 4 is in a stopped state. The priming solution (dialysate) supplied from the priming solution supply line Lc flows from the connection portion P of the arterial blood circuit 1 toward the distal end portion of the arterial blood circuit 1 and the distal end portion of the venous blood circuit 2. The priming solution flows into the venous air trap chamber 6 of the venous blood circuit 2, and the priming solution (dialysate) overflowing from the venous air trap chamber 6 is discharged outward by the overflow line L.

Then, it is determined in Step S2 whether or not a predetermined period of time elapses from when the overflow step S1 starts. In a case where the predetermined period of time elapses, the process proceeds to a circulation step S3. In the overflow step S1, in a case where the arterial air bubble detection device 7 or the venous air bubble detection device 8 does not detect air bubbles for a predetermined period of time, the process may proceed to the circulation step S3. As illustrated in FIG. 3, the circulation step S3 is performed in such a way that the control device 11 brings the electromagnetic valves V1 and V2 into an open state, brings the electromagnetic valves V3, V4, V5, and V6 into a closed state, and causes the blood pump 4 to perform reverse rotation. In this manner, the priming solution (dialysate) supplied in the overflow step S1 flows while being circulated in the arterial blood circuit 1, the venous blood circuit 2, and the blood flow route of the dialyzer 3.

Then, in Step S4, it is determined whether or not the arterial air bubble detection device 7 detects air bubbles. If the air bubbles are detected, the process returns to S1 so as to perform the overflow step again. As described above, until the arterial air bubble detection device 7 cannot detect the air bubbles, the overflow step S1 and the circulation step S3 are repeatedly performed. In the flow route of the arterial blood circuit 1, the venous blood circuit 2, and the blood flow route of the dialyzer 3, air is replaced with the priming solution (dialysate). In Step S4, it may be determined whether or not the venous air bubble detection device 8 detects the air bubbles.

On the other hand, if it is determined that the air bubbles are not detected in Step S4, a dialysate filling step S5 is performed. The dialysate filling step S5 is a so-called gas purging step, and is a step of filling the dialysate flow route of the dialyzer 3 with the dialysate at least by bringing the electromagnetic valves V3 and V6 into a closed state, bringing the electromagnetic valves V4 and V5 into an open state, and rotating the duplex pump 9. In the dialysate filling step S5, the other electromagnetic valves V1 and V2 may be brought into an open state or a closed state, and the blood pump 4 may be brought into an operating state or a stopped state.

Thereafter, it is determined in Step S6 whether or not a predetermined period of time elapses from when the dialysate filling step S5 starts. In a case where the predetermined period of time elapses, the process proceeds to a cleaning step S7. As illustrated in FIG. 4, the cleaning step S7 is performed in such a way that the control device 11 brings the electromagnetic valves V1 to V3 and V6 into an open state, brings the electromagnetic valves V4 and V5 into a closed state, and causes the blood pump 4 to perform forward rotation. In this case, rotation speed of the blood pump 4 is set to be smaller than a flow rate of the priming solution (dialysate) supplied from the priming solution supply line Lc. The priming solution supplied from the priming solution supply line Lc is adapted to flow to both the distal end side (connector c side) and the blood pump 4 side in the arterial blood circuit 1.

In this manner, the priming solution (dialysate) is supplied again from the priming solution supply line Lc to the blood circuit filled with the priming solution (dialysate) in the overflow step S1 and the circulation step S3. The priming solution flows by being divided in two directions from the connection portion P, and is discharged outward from the overflow line L. Accordingly, the blood circuit and the blood flow route of the dialyzer 3 can be cleaned. Then, it is determined in Step S8 whether or not the amount of the priming solution supplied from the priming solution supply line Lc reaches a predetermined amount. In a case where the amount reaches the predetermined amount, the process proceeds to an air purging step S9.

In the air purging step S9, as illustrated in FIG. 5, the control device 11 brings the electromagnetic valves V1 to V3 and V6 into an open state, and brings the electromagnetic valves V4 and V5 into a closed state (that is, each state of the electromagnetic valves V1 to V6 is maintained from the cleaning step S7). The control device 11 causes the blood pump 4 to perform reverse rotation. That is, the blood pump 4 is caused to perform the reverse rotation, and the overflow line L (priming solution discharge unit) and the priming solution supply line Lc are opened. While the priming solution (dialysate) is supplied from the priming solution supply line Lc, the priming solution (dialysate) is discharged from the overflow line L (priming solution discharge unit).

In this case, rotation speed of the blood pump 4 is set to be smaller than a flow rate of the priming solution (dialysate) supplied from the priming solution supply line Lc. The priming solution flowing into the venous air trap chamber 6 after being supplied from the priming solution supply line Lc is adapted to flow to both the dialyzer 3 side and the overflow line L side. That is, while the priming solution is supplied to and circulated in the blood circuit, the priming solution is discharged by the overflow line L. In this manner, the blood pump 4 is caused to perform reverse rotation so that supplying the priming solution from the priming solution supply line Lc is performed concurrently with discharging the priming solution from the overflow line L. Accordingly, air bubbles accumulated on the blood inlet 3*a* side of the dialyzer 3 can be moved to the arterial air trap chamber 5. Furthermore, the blood pump 4 is caused to perform the reverse rotation so as to move air inside the arterial air trap chamber 5 to the venous air trap chamber 6. In this manner, the air can be discharged outward via the overflow line L.

Then, in Step S10, it is determined whether or not a predetermined amount of the priming solution is supplied from the priming solution supply line Lc, or it is determined whether or not a predetermined period of time elapses from when the air purging step S9 starts. In a case where the predetermined amount of the priming solution is supplied or in a case where the predetermined period of time elapses, a series of steps for the priming is completed. In Step S10, it may be determined whether or not the arterial air bubble detection device 7 or the venous air bubble detection device 8 detects air bubbles. In a case where the arterial air bubble detection device 7 or the venous air bubble detection device 8 does not detect the air bubbles, a series of steps for the priming may be completed. After the priming, the distal end of the arterial blood circuit 1 and the distal end of the venous blood circuit 2 are disconnected from each other, and are respectively attached to the arterial puncture needle a and the venous puncture needle b so as to puncture a patient. In this manner, a step for blood purification treatment can start.

Next, priming in a blood purification apparatus according to a second embodiment of the present invention will be described with reference to a flowchart in FIG. 7. Each configuration of the blood circuit, the dialyzer, the dialysis apparatus main body, and the like is the same as that according to the first embodiment, and thus, description thereof will be omitted.

During the priming, similarly to the first embodiment, the blood inlet 3*a* of the dialyzer 3 is brought into a state of facing upward (fixed by a fixing device (not illustrated)), and the connector c and the connector d are connected to each other so that the mutual flow routes communicate with each other. If the priming starts, the overflow step S1 (refer to FIG. 2) is first performed, and it is determined in Step S2 whether or not a predetermined period of time elapses. In a case where the predetermined period of time elapses, the air purging step S3 is performed (refer to FIG. 5).

Then, it is determined in Step S4 whether or not the arterial air bubble detection device 7 detects air bubbles. If the air bubbles are detected, the process returns to S1 so as to perform the overflow step again. In Step S4, it may be determined whether or not the venous air bubble detection device 8 detects the air bubbles. As described above, until the arterial air bubble detection device 7 cannot detect the air bubbles, the overflow step S1 and the air purging step S3 are repeatedly performed. Accordingly, the air bubbles accumulated on the blood inlet 3*a* side of the dialyzer 3 can be moved to the arterial air trap chamber 5. Furthermore, the blood pump 4 is caused to perform the reverse rotation so as to move air inside the arterial air trap chamber 5 to the venous air trap chamber 6. In this manner, the air can be discharged outward via the overflow line L.

On the other hand, if it is determined in Step S4 that the air bubbles cannot be detected, the dialysate filling step S5 similar to that according to the first embodiment is performed. Thereafter, it is determined in Step S6 whether or not a predetermined period of time elapses from when the dialysate filling step S5 starts. In a case where the predetermined period of time elapses, the process proceeds to the cleaning step S7 (refer to FIG. 4). Then, it is determined in Step S8 whether or not an amount of the priming solution supplied from the priming solution supply line Lc reaches a predetermined amount. In a case where the amount reaches the predetermined amount, a series of steps for the priming is completed.

Next, a blood purification apparatus according to a third embodiment of the present invention will be described.

Similarly to the first embodiment, the blood purification apparatus according to the present embodiment includes a dialysis apparatus for performing dialysis treatment. As illustrated in FIGS. 8 to 12, the blood purification apparatus is mainly configured to include the blood circuit that has the arterial blood circuit 1 and the venous blood circuit 2, the dialyzer 3 (blood purification device) that is interposed between the arterial blood circuit 1 and the venous blood circuit 2 so as to purify blood flowing in the blood circuit, the peristaltic blood pump 4 that is arranged in the arterial blood circuit 1, the arterial air trap chamber 5 that is connected to the arterial blood circuit 1, the venous air trap chamber 6 that is connected to the venous blood circuit 2, a priming solution supply line Ld, the overflow line L functioning as the priming solution discharge unit, the electromagnetic valve V6 functioning as the first valve device, the electromagnetic valve V3 functioning as the second valve device, and the control device 11. The same reference numerals are given to configuration elements which are the same as those according to the first embodiment, and thus, description thereof will be omitted.

A distal end of the priming solution supply line Ld is connected to the blood circuit (connection portion P between the electromagnetic valve V1 and the blood pump 4 in the arterial blood circuit 1) so that the priming solution (physiological saline solution) can be supplied into the blood circuit. According to the present embodiment, a proximal end thereof is connected to an accommodation device 12 (a so called "physiological saline solution bag"). In addition, the electromagnetic valve V6 functioning as the first valve device which can selectively close and open a flow route thereof is arranged in an intermediate portion of the priming solution supply line Ld, and an air trap chamber for priming solution 13 is connected to the intermediate portion.

The accommodation device 12 includes a flexible and transparent container, and can accommodate a predetermined amount of the physiological saline solution (priming solution). For example, the accommodation device 12 is attached to a distal end of a pole (not illustrated) which is arranged to protrude from the dialysis apparatus main body. The electromagnetic valve V6 is brought into an open state so as to open a flow route thereof. In this manner, the physiological saline solution inside the accommodation device 12 is supplied to the blood circuit by using its own weight. The supply (dripping) of the physiological saline solution (priming solution) is visible by the air trap chamber for priming solution 13.

Here, according to the present embodiment, a configuration is adopted in which, before priming, a liquid accumulation generating step is performed on the air trap chamber for priming solution 13 as illustrated in FIG. 13 and the priming is performed thereafter.

First, as illustrated in FIG. 8, the blood inlet 3*a* of the dialyzer 3 is brought into a state of facing upward (fixed by a fixing device (not illustrated)), and the connector c and the connector d are connected to each other so that the mutual flow routes communicate with each other. Thereafter, the control device 11 brings the electromagnetic valves V2 and V6 into an open state, and brings the electromagnetic valves V1 and V3 to V5 into a closed state. The control device 11 causes the blood pump 4 to perform forward rotation, thereby performing a liquid accumulation generating step Sa. In this manner, the physiological saline solution (priming solution) inside the accommodation device 12 can be introduced to the connection portion P of the arterial blood circuit 1 via the priming solution supply line Ld.

Then, it is determined in Step Sb whether or not the blood pump 4 performs forward rotation a predetermined number of times (for example, five times). If the number of rotations reaches the predetermined number of times, the process proceeds to a liquid accumulation generating step Sc. In the liquid accumulation generating step Sc, as illustrated in FIG. 9, the control device 11 brings the electromagnetic valves V2 and V6 into an open state, brings the electromagnetic valves V1 and V3 to V5 into a closed state (maintains a state in the liquid accumulation generating step Sa), and causes the blood pump 4 to perform reverse rotation. In this manner, liquid accumulation is generated inside the air trap chamber for priming solution 13 by the physiological saline solution.

In the blood purification apparatus according to the present embodiment, after the above-described liquid accumulation generating step is completed, the priming according to the first embodiment (refer to FIG. 6) or the priming according to the second embodiment (refer to FIG. 7) is performed. However, in a case of the present embodiment, in the cleaning step, as illustrated in FIG. 10, the control device 11 brings the electromagnetic valves V1 to V3 and V6 into an open state, brings the electromagnetic valves V4 and V5 into a closed state, and stops the blood pump 4. Thereafter, as illustrated in FIG. 11, the control device 11 brings the electromagnetic valves V3 and V6 into an open state, brings the electromagnetic valves V1, V2, V4, and V5 into a closed state, and causes the blood pump 4 to perform forward rotation. The electromagnetic valves V1 and V2 may be brought into an open state.

In addition, as illustrated in FIG. 12, the air purging step according to the present embodiment is performed in such a way that the control device 11 brings the electromagnetic valves V1 to V3 and V6 into an open state, brings the electromagnetic valves V4 and V5 into a closed state, and causes the blood pump 4 to perform reverse rotation. According to the air purging step, supplying the priming solution from the priming solution supply line Ld is performed concurrently with discharging the priming solution from the overflow line L. Accordingly, air bubbles accumulated on the blood inlet 3*a* side of the dialyzer 3 can be moved to the arterial air trap chamber 5. Furthermore, the blood pump 4 is caused to perform the reverse rotation so as to move air inside the arterial air trap chamber 5 to the venous air trap chamber 6. In this manner, the air can be discharged outward via the overflow line L.

Next, a blood purification apparatus according to a fourth embodiment of the present invention will be described.

Similarly to the first embodiment, the blood purification apparatus according to the present embodiment includes a dialysis apparatus for performing dialysis treatment. As illustrated in FIG. 14, the blood purification apparatus is mainly configured to include the blood circuit that has the arterial blood circuit 1 and the venous blood circuit 2, the dialyzer 3 (blood purification device) that is interposed between the arterial blood circuit 1 and the venous blood circuit 2 so as to purify blood flowing in the blood circuit, the peristaltic blood pump 4 that is arranged in the arterial blood circuit 1, the arterial air trap chamber 5 that is connected to the arterial blood circuit 1, the venous air trap chamber 6 that is connected to the venous blood circuit 2, a priming solution supply line Le, the overflow line L functioning as the priming solution discharge unit, the electromagnetic valve V6 functioning as the first valve device, the electromagnetic valve V3 functioning as the second valve device, and the control device 11. The same reference numerals are given to configuration elements which are the same as those according to the first embodiment, and thus, description thereof will be omitted.

A distal end of the priming solution supply line Le is connected to the blood circuit (connection portion P between the electromagnetic valve V2 and the venous air trap chamber 6 in the venous blood circuit 2) so that the priming solution (dialysate) can be supplied into the blood circuit. According to the present embodiment, a proximal end thereof is connected between the duplex pump 9 and the electromagnetic valve V4 in the dialysate introduction line La. In addition, the electromagnetic valve V6 functioning as the first valve device which can selectively close and open a flow route thereof is arranged in an intermediate portion of the priming solution supply line Le.

The electromagnetic valve V6 is brought into an open state while the electromagnetic valve V4 is brought into a closed state, and the duplex pump 9 is rotated. In this configuration, the dialysate of the dialysate introduction line La is supplied to the venous blood circuit 2 via the priming solution supply line Le. As described above, according to the present embodiment, the dialysate flowing in the dialysate introduction line Le is supplied to the blood circuit (venous blood circuit 2) as the priming solution.

Here, in the blood purification apparatus according to the present embodiment, the priming according to the first embodiment (refer to FIG. 6) or the priming according to the second embodiment (refer to FIG. 7) is performed. However, in a case of the present embodiment, in the air purging step, as illustrated in FIG. 14, the distal end of the arterial blood circuit 1 and the distal end of the venous blood circuit 2 are not connected to each other, and are brought into a mutually open state. The control device 11 brings the electromagnetic valves V1, V2, and V6 into an open state, brings the electromagnetic valves V3 to V5 into a closed state, and causes the blood pump 4 to perform reverse rotation. In this case, rotation speed of the blood pump 4 is set to be smaller than a flow rate of the priming solution (dialysate) supplied from the priming solution supply line Le. The priming solution supplied from the priming solution supply line Le is adapted to flow to both the dialyzer 3 side and the distal end side (connector d side) of the venous blood circuit 2.

According to the air purging step, supplying the priming solution from the priming solution supply line Le is performed concurrently with discharging the priming solution from the overflow line L. Accordingly, air bubbles accumulated on the blood inlet 3*a* side of the dialyzer 3 can be moved to the arterial air trap chamber 5. Furthermore, the blood pump 4 is caused to perform the reverse rotation so as to move air inside the arterial air trap chamber 5 to the distal end side (connector c side) of the arterial blood circuit 1. In this manner, the air can be discharged outward via the overflow line L. A configuration may be adopted in which the electromagnetic valve V3 is brought into an open state so that the priming solution flowing into the venous air trap chamber 6 after being supplied from the priming solution supply line Le flows to both the dialyzer 3 side and the overflow line L side. In this case, the blood pump 4 is caused to perform reverse rotation so as to move the air to the venous air trap chamber 6. In this manner, the air can be discharged outward via the overflow line L.

According to the above-described first to fourth embodiments, during the priming, the air purging step is performed by causing the blood pump 4 to perform reverse rotation, and opening the overflow line L (priming solution discharge unit) and the priming solution supply lines (Lc, Ld, and Le) so as to discharge the priming solution from the overflow line L (priming solution discharge unit) while supplying the priming solution from the priming solution supply lines (Lc, Ld, and Le). Therefore, the air bubble purging of the dialyzer 3 (blood purification device) can be reliably performed while workability is maintained during the priming.

In addition, according to the above-described first to fourth embodiments, the arterial air trap chamber 5 is connected between the blood pump 4 and the dialyzer 3 (blood purification device) in the arterial blood circuit 1. Accordingly, air bubbles accumulated near the blood inlet 3*a* of the dialyzer 3 can be accommodated in the arterial air trap chamber 5, and air bubbles excessively flowing into the arterial air trap chamber 5 can be discharged together with the priming solution from the overflow line L (priming solution discharge unit).

Furthermore, according to the above-described first to fourth embodiments, the venous air trap chamber 6 is connected to the venous blood circuit 2, and the priming solution discharge unit includes the overflow line L which extends from the upper portion of the venous air trap chamber 6. Accordingly, the priming solution supplied from the priming solution supply lines (Lc, Ld, and Le) can be discharged outward by utilizing the venous air trap chamber 6 and the overflow line L which are generally disposed in the blood circuit.

According to the above-described first to fourth embodiments, all of the priming steps are performed in a state where the blood inlet 3*a* of the dialyzer 3 faces upward. Accordingly, it is not necessary to carry out work for vertically inverting the dialyzer 3. Thus, the priming step can be easily automated, and the air bubble purging can be quickly and reliably performed in the dialyzer 3. In addition, according to the above-described first to fourth embodiments, priming work can be carried out under a series of control by the control device 11. Accordingly, the priming can be easily automated, and the amount work to be carried out by a worker can be remarkably reduced. Furthermore, operations according to the present embodiments can be performed by changing control content of the control device 11. Therefore, it is possible to provide the blood purification apparatus (dialysis apparatus) according to the present invention while the blood purification apparatus including the existing blood circuit is utilized without any substantial change.

Hitherto, the present embodiments have been described. However, without being limited thereto, for example, the present invention is applicable to an apparatus which does not have the arterial air trap chamber 5 or the venous air trap chamber 6. In addition, as long as the priming solution (dialysate or physiological saline solution) supplied by the priming solution supply line can be discharged outward after the priming solution overflows from the blood circuit, a unit (priming solution discharge unit) formed at other positions may be employed instead of the overflow line L. Furthermore, without being limited to the dialysate or the physiological saline solution, the priming solution supplied by the priming solution supply line may employ other liquids. The present embodiments are applied to a dialysis apparatus used during dialysis treatment, but may be applied to other apparatuses which can extracorporeally circulate and purify blood of a patient (for example, blood purification apparatuses which are used in a blood filtration dialysis method, a blood filtration method, and AFBF, plasma adsorption apparatuses, and the like).

As long as there are provided a blood purification apparatus and a priming method thereof in which, during the priming, an air purging step is performed by causing a blood pump to perform reverse rotation, and opening the priming solution discharge unit and a priming solution supply line so as to discharge a priming solution from a priming solution discharge unit while supplying the priming solution from the priming solution supply line, the present invention is also applicable to other forms and uses.

REFERENCE SIGNS LIST

1 ARTERIAL BLOOD CIRCUIT
2 VENOUS BLOOD CIRCUIT

3 DIALYZER (BLOOD PURIFICATION DEVICE)
4 BLOOD PUMP
5 ARTERIAL AIR TRAP CHAMBER
6 VENOUS AIR TRAP CHAMBER
7 ARTERIAL AIR BUBBLE DETECTION DEVICE
8 VENOUS AIR BUBBLE DETECTION DEVICE
9 DUPLEX PUMP
10 ULTRAFILTRATION PUMP
11 CONTROL DEVICE
12 ACCOMMODATION DEVICE
13 AIR TRAP CHAMBER FOR PRIMING SOLUTION
La DIALYSATE INTRODUCTION LINE
Lb DIALYSATE DISCHARGE LINE
Lc, Ld, Le PRIMING SOLUTION SUPPLY LINE
L OVERFLOW LINE (PRIMING SOLUTION DISCHARGE UNIT)
V3 ELECTROMAGNETIC VALVE (SECOND VALVE DEVICE)
V6 ELECTROMAGNETIC VALVE (FIRST VALVE DEVICE)

The invention claimed is:

1. A blood purification apparatus comprising:

A blood circuit that includes an arterial blood circuit and a venous blood circuit, and that can extracorporeally circulate blood of a patient from a distal end of the arterial blood circuit to a distal end of the venous blood circuit;

A blood purification device that purifies the blood flowing in the blood circuit by being interposed between the arterial blood circuit and the venous blood circuit of the blood circuit, that has a blood flow route through which the blood of the patient flows via a blood purification membrane for purifying the blood and a dialysate flow route through which a dialysate flows, and that has a blood inlet which can introduce the blood to the blood flow route, a blood outlet which can draw out the blood from the blood flow route, a dialysate inlet which can introduce the dialysate to the dialysate flow route, and a dialysate outlet which can discharge the dialysate from the dialysate flow route;

A blood pump that is arranged in the arterial blood circuit, and that is capable of forward rotation which rotates in a direction of circulating the blood during blood purification treatment and reverse rotation which rotates in a direction opposite to the direction of circulating the blood during the blood purification treatment;

A priming solution supply line that is connected to the blood circuit, and that can supply a priming solution in to the blood circuit;

A priming solution discharge unit that can cause the priming solution supplied by the priming solution supply line to overflow from the blood circuit so as to be discharged outward;

A first valve device that can selectively close or open the priming solution supply line;

A second valve device that can selectively close or open the priming solution discharge unit;

A venous air trap chamber connected to the venous blood circuit, the priming solution discharge unit including an overflow line which extends from an upper portion of the venous air trap chamber; and A control device that can control the blood pump, the first valve device, and the second valve device, wherein priming is performed in a state where the blood inlet of the blood purification device faces upward, and wherein during the priming, the control device performs an air purging step of causing the blood pump to perform the reverse rotation, and opening the priming solution discharge unit and the priming solution supply line so as to discharge the priming solution and air bubbles from the priming solution discharge unit, while supplying the priming solution from the priming solution supply line; and wherein the supplying the priming solution from the priming solution supply line is performed concurrently with discharging the priming solution from an overflow line.

2. The blood purification apparatus according to claim 1, wherein an arterial air trap chamber is connected between the blood pump and the blood purification device in the arterial blood circuit.

3. A priming method of a blood purification apparatus comprising:

A blood circuit that includes an arterial blood circuit and a venous blood circuit, and that can extracorporeally circulate blood of a patient from a distal end of the arterial blood circuit to a distal end of the venous blood circuit;

A blood purification device that purifies the blood flowing in the blood circuit by being interposed between the arterial blood circuit and the venous blood circuit of the blood circuit, that has a blood flow route through which the blood of the patient flows via a blood purification membrane for purifying the blood and a dialysate flow route through which a dialysate flows, and that has a blood inlet which can introduce the blood to the blood flow route, a blood outlet which can draw out the blood from the blood flow route, a dialysate inlet which can introduce the dialysate to the dialysate flow route, and a dialysate outlet which can discharge the dialysate from the dialysate flow route;

A blood pump that is arranged in the arterial blood circuit, and that is capable of forward rotation which rotates in a direction of circulating the blood during blood purification treatment and reverse rotation which rotates in a direction opposite to the direction of circulating the blood during the blood purification treatment;

A priming solution supply line that is connected to the blood circuit, and that can supply a priming solution in to the blood circuit;

A priming solution discharge unit that can cause the priming solution supplied by the priming solution supply line to overflow from the blood circuit so as to be discharged outward;

A first valve device that can selectively close or open the priming solution supply line;

A second valve device that can selectively close or open the priming solution discharge unit; and A venous air trap chamber connected to the venous blood circuit, the priming solution discharge unit includes an overflow line which extends from an upper portion of the venous air trap chamber;

Wherein priming is performed in a state where the blood inlet of the blood purification device faces upward, and Wherein during the priming, an air purging step is performed by causing the blood pump to perform the reverse rotation, and opening the priming solution discharge unit and the priming solution supply line so as to discharge the priming solution and air bubbles from the priming solution discharge unit while supplying the priming solution from the priming solution supply line; and Wherein the supplying the priming solution from the priming solution supply line is performed concurrently with discharging the priming solution from an overflow line.

4. The priming method of the blood purification apparatus according to claim 3, wherein an arterial air trap chamber is connected between the blood pump and the blood purification device in the arterial blood circuit.

5. The blood purification apparatus according to claim 1, wherein a distal end of the priming solution supply line is connected to the blood circuit at a connection portion between a valve device and the blood pump in the arterial blood circuit and a proximal end of the priming solution supply line is connected to a dialysate introduction line.

6. The priming method of the blood purification apparatus according to claim 3, wherein a distal end of the priming solution supply line is connected to the blood circuit at a connection portion between a valve device and the blood pump in the arterial blood circuit and a proximal end of the priming solution supply line is connected to a dialysate introduction line.

7. The blood purification apparatus according to claim 1, wherein a distal end of the priming solution supply line is connected to the blood circuit at a connection portion between a valve device and the blood pump in the arterial blood circuit and a proximal end of the priming solution supply line is connected to an accommodation device including priming solution.

8. The priming method of the blood purification apparatus according to claim 3, wherein a distal end of the priming solution supply line is connected to the blood circuit at a connection portion between a valve device and the blood pump in the arterial blood circuit and a proximal end of the priming solution supply line is connected to an accommodation device including priming solution.

9. The blood purification apparatus according to claim 1, wherein a distal end of the priming solution supply line is connected to the blood circuit at a connection portion between a valve device and the venous air trap chamber in the venous blood circuit and a proximal end of the priming solution supply line is connected to a dialysate introduction line.

10. The priming method of the blood purification apparatus according to claim 3, wherein a distal end of the priming solution supply line is connected to the blood circuit at a connection portion between a valve device and the venous air trap chamber in the venous blood circuit and a proximal end of the priming solution supply line is connected to a dialysate introduction line.

* * * * *